US009566041B2

(12) United States Patent
Christensen et al.

(10) Patent No.: US 9,566,041 B2
(45) Date of Patent: *Feb. 14, 2017

(54) ADHESIVE PATCH HAVING MULTIPLE ACOUSTIC SENSORS FOR MONITORING ACOUSTIC SIGNALS

(71) Applicant: Acarix A/S, Kgs Lyngby (DK)

(72) Inventors: Claus Bo Voge Christensen, Snekkersten (DK); Weimin Rong, Bagsvaerd (DK)

(73) Assignee: Acarix A/S, Kgs Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,593

(22) Filed: Dec. 12, 2014

(65) Prior Publication Data

US 2015/0099998 A1    Apr. 9, 2015

Related U.S. Application Data

(63) Continuation of application No. 12/809,564, filed as application No. PCT/DK2008/050310 on Dec. 16, 2008, now Pat. No. 8,911,383.

(30) Foreign Application Priority Data

Dec. 20, 2007    (DK) .................. 2007 01831

(51) Int. Cl.
*A61B 7/00*    (2006.01)
*A61B 7/04*    (2006.01)
*A61B 5/00*    (2006.01)

(52) U.S. Cl.
CPC ............. *A61B 7/04* (2013.01); *A61B 5/0002* (2013.01); *A61B 5/6833* (2013.01); *A61B 7/006* (2013.01); *A61B 2562/0204* (2013.01)

(58) Field of Classification Search
CPC ........... A61B 5/0002; A61B 7/00; A61B 7/04; A61B 7/026
USPC ............... 600/300, 515, 586, 509, 544, 546, 481,600/484, 488, 502, 529, 528; 381/151; 128/903
See application file for complete search history.

(56) References Cited

U.S. PATENT DOCUMENTS

| 4,995,473 A | 2/1991 | Packard |
| 5,595,188 A | 1/1997 | Kassal |
| 5,853,005 A | 12/1998 | Scanlon |
| 6,061,584 A | 5/2000 | Lovejoy et al. |

(Continued)

FOREIGN PATENT DOCUMENTS

| EP | 262976 A2 | 4/1988 |
| WO | 2004078038 A1 | 9/2004 |

OTHER PUBLICATIONS

International Search Report for PCT/DK2008/050310, Dated Apr. 1, 2009.

(Continued)

*Primary Examiner* — Michael C. Stout
*Assistant Examiner* — Megan Leedy
(74) *Attorney, Agent, or Firm* — Fulwider Patton LLP

(57) ABSTRACT

An adhesive patch for monitoring acoustic signals from a human or animal body, comprising a skin contact surface, converting means for recording both body acoustic signals and environmental acoustic noise, reducing the body signals by the recorded noise, and providing a first electric output signal. The patch also comprising an adhesive element and a compression structure for attaching the converting means to the skin surface. The patch further comprises transmitting means for transmitting the output signal to a peripheral device.

4 Claims, 3 Drawing Sheets

(56) References Cited

U.S. PATENT DOCUMENTS

| | | |
|---|---|---|
| 6,368,286 B1 | 4/2002 | Whitman et al. |
| 2006/0155173 A1 | 7/2006 | Anttila et al. |
| 2006/0224055 A1 | 10/2006 | Kermani et al. |
| 2007/0165885 A1 | 7/2007 | Chou |
| 2007/0255153 A1 | 11/2007 | Kumar et al. |
| 2007/0276270 A1 | 11/2007 | Tran |

OTHER PUBLICATIONS

International Preliminary Report on PCT/DK2008/050310, Dated Mar. 22, 2010.

ADHESIVE PATCH HAVING MULTIPLE ACOUSTIC SENSORS FOR MONITORING ACOUSTIC SIGNALS

RELATED APPLICATIONS

This is a continuation application of application Ser. No. 12/809,564, filed Oct. 20, 2010, which claims priority to PCT/DK2008/050310, filed Dec. 16, 2008, and Danish Application No. PA2007 01831, filed Dec. 20, 2007, all of which are incorporated herein by reference.

FIELD OF THE INVENTION

The present invention relates to the field of adhesive patches, which can detect and record acoustic signals from the body.

BACKGROUND

A widely used tool used by medical professionals for performing relatively simple diagnostic tasks is the stethoscope, which is used to listen to a variety of internal bodily functions through the skin of a human or animal patient. The conventional stethoscope has been used for hundreds of years for assisting the medical professional in providing diagnostics for a wide range of illnesses. A significant problem when using a conventional stethoscope is that the sound captured by the stethoscope is not actively amplified, only conveyed via flexible or stiff tubular material to the ears of the medical professional, which means that very subtle sounds within the body cannot be identified using the stethoscope in real time.

One way of solving this problem is through the invention of the electronic digital stethoscope, which is capable of amplifying the sound levels from the body and processing the sound for optimal listening, such that a medical professional is capable of listening to sounds, which are hardly conceivable using a conventional stethoscope. The traditional digital stethoscope and the conventional stethoscope both have the same drawback, which is that a medical professional is required to listen to the sounds collected by the stethoscope in real time, and make a judgment based on what he hears. However, recent digital stethoscopes have been provided with the capability to store a few seconds of recorded sound, such that the medical professional may choose to listen again to the sounds stored in the digital stethoscope.

US Patent Application No. US 2007/0276270 attempts to solve this problem by describing a health care monitoring system, which describes one or more wireless nodes forming a wireless mesh network, where the mesh network communicates with a base station in the form of a computer server, where the nodes transmit patient data to the base station to detect a heart attack or a stroke attack.

One described embodiment of the aforementioned system describes collection of wireless nodes having different functions where one wireless node is an electronic stethoscope where heart sounds are transmitted from the wireless node to a base station, using sounds recorded from the wrist of the patient. The collection of wireless nodes is required to communicate continuously with the base station when in range. A serious drawback to this health care monitoring system is that the wireless node has to communicate the signals to a base station to be capable of performing any analyzing tasks. This means that the user or a health care professional is required to communicate with the base station to obtain or access any information about the recorded patient data. Furthermore, as the wireless communication is continuously with the base station when in range, the power consumption is significant, as the collection of node would have to check continuously if the base station is in range and receive a confirmation thereof in addition to the continuous data transmission of the recorded patient data.

Coronary artery disease (CAD) is a continuously increasing threat to the public health in western society, where tobacco smoking, increased stress, lack of exercise, fat saturated diets, obesity, etc. are reported to be significant direct or indirect risk factors for the development of blockages in the coronary arteries, resulting in coronary artery disease. Currently, the present methods for assisting in the diagnostics and/or diagnosis of CAD are expensive and require complicated equipment, such as an electrocardiogram, nuclear scanning, angiography or coronary angiography, CAT scans and MRI scans. Furthermore, these methods require that the subject spend a considerable amount of time in hospital laboratories.

The execution of the previously mentioned methods may be very expensive, which means that the methods are rarely used for preventive diagnostics and subjects are usually subjected to CAD diagnostics subsequent to physical problems indicating the presence of CAD, such as chest pains, etc.

Therefore, there is a need for an improvement in monitoring the physical signs of CAD, using acoustic signals from the human or animal body, where the acoustic signals are selectively or continuously recorded and/or transmitted to a peripheral device. The selective transmission means that normal signals would not be transmitted while abnormal signals could trigger a transmission.

SUMMARY OF THE INVENTION

An object of the present invention is to provide an adhesive patch, which can continuously monitor acoustic signals from the human body.

Another object of the present invention is to provide an adhesive patch, which can alert the user if the monitored acoustic signals change in a predefined manner from predefined normal acoustic signals.

A further object of the present invention is to provide an adhesive patch that can process the acoustic signals in a predefined manner and compare the processed signals to standard values and store the acoustic signals for subsequent transmission to a peripheral device.

A yet further object of the present invention is to provide an adhesive patch that is suitable for detecting early signals of coronary artery disease.

The present invention discloses an adhesive patch for monitoring acoustic signals from a human or animal body, comprising a skin contact surface; converting means for recording the acoustic signals and converting it to a first electric output signal; an adhesive element for attaching the converting means to the skin surface; transmitting means for transmitting the electric output signal to a peripheral device; and means for managing the pressure between the converting means and the skin contacting surface.

The adhesive patch is provided with an adhesive layer on the skin contact surface, where the adhesive layer ensures that the patch stays in place after it has been placed onto the skin surface of a user. It has been shown during testing of one embodiment that if the acoustic recordings are obtained while the converting means are held in position by the user or a healthcare professional, which often is done using an analog or digital stethoscope, the converting means collect a mechanical noise which is caused by minute vibrations originating from the hand or the human extremity which holds it in place. Although it appears that some people have a very steady hand, it is physically impossible to remove all vibrations as skeletal muscles are stimulated using periodical nerve signals, which cause very small vibration in the muscle as each muscle fiber contracts.

The vibration caused by the hand becomes a significant noise factor when the converting means are held in position using the arm and/or the hand for recording the acoustic signals from the body and the converting means are very sensitive and capable of recording extremely vague signals. This type of noise can be reduced drastically using an embodiment where the converting means are adhered to the skin surface using an adhesive patch, such that the converting means are not affected by vibrations in the hand of the medical professional.

It should be understood that the term 'acoustic' should be interpreted broadly as a difference, typically a change, in pressure, which for example is conveyed through the air and/or the human or animal body from a target area, e.g. a coronary artery, to a detecting unit, for example the human ear or the converting means. For example the above described mechanical noise caused by minute vibration originating from the hand is not audible to the human ear without being processed, e.g. by amplification and/or frequency manipulation.

Another advantage of adhering the converting means to the skin surface is that the user can wear the adhesive patch for a longer period of time, such that acoustic signals may be recorded over a longer time period, if deemed necessary for diagnostic purposes.

The recorded acoustic signals are converted into a first electric output signal, which may be transmitted directly via wireless or wired transmitting means to a peripheral device. It should be understood that a peripheral device is a stand-alone unit separate from the patch, for example a personal computer (PC), a mobile telephone or a PDA (personal digital assistant). In the peripheral device the signals may be further processed, or used unprocessed by a medical professional for assessing the acoustic content of the signals by listening to it using a loudspeaker, headphones or similar electrical signal converting means.

The acoustic signals are recorded by placing the converting means, or the microphone, in direct contact with the skin surface of the user or by positioning an acoustic conducting layer between the converting means and the skin surface, the acoustic conducting layer functioning as a means for sound propagation. It has been discovered that any change in pressure between the converting means and the skin surface, may influence and/or reduce the transmission of the sound between the skin surface and the converting means. The acoustic conductivity, transmission and/or contact between the conducting means and the skin surface is optimized by maintaining the pressure between the converting means and the skin surface as stable as possible, i.e. that the pressure does not vary significantly during the use time of the adhesive patch or that the pressure applied is significantly higher than any variation in pressure.

This may be achieved by having a resilient material that supports the side of the converting means that faces away from the skin surface and maintains the converting means at a constant pressure to the skin surface, and if there are any changes in the force that is applied from the converting means to the skin or from the skin surface to the converting means, the resilient material absorbs at least the majority of the force but maintains the pressure between the skin surface and the converting means.

Another means for the management of pressure between the converting means and the skin surface may be to provide a compression structure at the skin contacting surface. The compression structure may be in the form of one or more protrusions that project out from the skin contacting surface. The protrusions may form a circle, an ellipse or any suitable shape in a closed line where the converting means is placed inside the closed line shape, or may be in the form of a number of suitably placed protrusions that are positioned close to and/or around the converting means.

When the skin contacting surface of the adhesive patch is placed on the skin, the protrusions apply an increased pressure onto the areas of the skin which are in contact with the protrusions and inside the area that is defined by the protrusions. This means that while the skin contacting surface of the adhesive patch maintains its contact with the adhesive patch, the skin surface inside the area defined by the protrusions maintains an increased tension. The tension of the skin surface does not vary significantly when the user moves or changes his/her posture as the compression structure maintains the tension of the skin inside the area defined by the protrusions. Within the skin contacting area defined by the area in a inwards radial direction from the protrusions, an acoustic medium can be applied to increase the tension at the skin surface further.

By positioning the conversion means onto the skin surface inside the area defined by the protrusions, such that the conversion means maintain its relative position in all directions with regards to the protrusions, it is ensured that the pressure of the converting means and the tension of the skin surface are managed and maintained during the use of the adhesive patch and thus the pressure between the converting means and the skin surface is managed effectively.

Another means for managing the pressure between the converting means and the skin surface may be to position the converting means inside a pressure cavity arranged in the adhesive patch. The skin contacting surface of the adhesive patch operates as the gas and/or liquid impermeable barrier between the adhesive patch and the skin surface. The pressure cavity may comprise an external wall which creates a gas- and/or liquid impermeable barrier to the atmosphere, which ensures that any gas or liquid contained or introduced into the cavity may be sealed inside the cavity. The adhesive patch may be provided with a one and/or two way valve which may be used to introduce or remove gas and/or liquids into the cavity to manage the pressure inside the cavity. The converting means may be placed inside the pressure cavity providing a direct or indirect contact with the skin surface of the user, where the pressure inside the cavity would ensure that any movement or change in the user's posture would not alter the pressure between the converting means and the skin surface. In one embodiment of the present invention the patch may further comprise processing means for processing the first electric output signal and converting it to at least a second electric output signal. For this purpose, the patch may be provided with processing means in the form of a microprocessor, microcontroller, A/D converter, digital signal processor and/or the necessary electrical circuitry such that the acoustic recording may be partly processed within the adhesive patch into a second electric output signal.

In the context of the present invention the term partly processed acoustic signal means an acoustic signal which may be processed with analog or digital signal processing in the form of filtering, analog to digital conversion digital or analog amplification, differential amplification, voltage amplification, output amplification and similar signal processing methods.

In one embodiment of the present invention the patch may further comprise analyzing means for processing the first or the second electric output signal and converting it to a third electric output signal. This means that the recorded acoustic signal may be fully processed within the adhesive patch.

The term fully processed acoustic signal means in the context of the present application an acoustic signal that has been fully processed within the adhesive patch, such that all signal-processing steps, which are deemed necessary to provide an indication of an abnormal signal, are taken. The signal processing steps are similar to the abovementioned steps defined in context of the partly processed acoustic signal. Additionally, the fully processed signal has been processed into values or a mathematical representation, which may be compared to standard values or fed into a mathematical model such that the processing means can be instructed to indicate if there are some unusual elements in the recorded acoustic signal.

In one embodiment of the present invention the processing means can statistically determine in what way the recorded signals deviate from the predefined standard values. If the adhesive patch uses standard values for comparison purposes, the standard values are selected based on which body acoustic signals are to be monitored and what ailment is to be monitored, as acoustic heart signals and acoustic respiratory signals are not suitable for comparison.

In one embodiment of the present invention the patch may further comprise storing means for storing at least one of the first, second or third electric output signals. This means that a health care professional can review parts of or all of the recorded acoustic signals after a user has been wearing the adhesive patch for monitoring purposes for a period of time. This also means that the user may not be required to be in a clinic when a monitoring task is being performed. The user might be provided with one or more patches and subsequently return to his normal routine wherein the adhesive patch is recording acoustic signals from the body while the user is acting in his normal fashion.

In one embodiment of the present invention the converting means may include at least one microphone, where the microphone is used to record the acoustic signals from the body. The microphone produces the first electrical output signal which may be stored within the adhesive patch, transmitted to a peripheral device, processed and/or analysed within the adhesive patch. In another embodiment of the present invention the converting means may include at least two microphones, where the first microphone is used to record the acoustic signals from the body and the at least second microphone is used to record environmental noise signals. By using two microphones, which are recording acoustic signals synchronously, the noise signal acquired from the second microphone can be used to remove the environmental noise recorded by the first microphone, which ideally reduces the noise level significantly and the remaining acoustic signal is the primary acoustic signal from the body, which is interesting for the diagnostic procedure.

A number of different types of microphones may be used for the purpose of recording acoustic signals from the body, where in one embodiment the at least one microphone may be a silicon microphone and in another embodiment the at least one microphone may be a pressure sensitive contact microphone. In alternative embodiments of the present invention where the adhesive patch includes more than one microphone, the microphones may be of different types. This might be advantageous as one type of microphone might be better suited for noise recording and another type might be better suited for the recording of acoustic signals from the body. It is obvious to the skilled person based on the teachings of the present invention that any type of microphone suited for recording noise, acoustic signals from the body or similar might be used in the adhesive patch of the present invention.

In an attempt to increase the quality of the acoustic recording of acoustic signals from the body, the adhesive patch may further comprise sound focusing means. The sound focusing means may be used to collect acoustic signals from a skin surface area that is larger than the collecting area of the converting means. The sound focusing means focus the acoustic signals towards one or more collecting areas, as might be done with a funnel like structure where the wide end collects the acoustic signals and gathers the acoustic signals in the narrow end. By adding sound focusing means the converting means are subjected to more acoustic signals than when directly using the converting means. This increases the sensitivity of the converting means and the acoustic patch is capable of acquiring more subtle or vague sounds than when not using sound focusing means.

In one embodiment of the present invention the sound focusing means may include a bell shaped compartment, where the converting means are positioned at a central position of the compartment. The bell shaped compartment allows the collected sound waves to bounce of the walls and reflect in a direction towards the converting means.

In another embodiment of the present invention the focusing means may include a diaphragm, where the diaphragm vibrates when the diaphragm is subjected to sound waves or vibrations due to pressure difference affecting the skin surface area in communication with the diaphragm. A diaphragm operates as a filter as the physical size of the diaphragm affects the responsiveness of the diaphragm.

In order to reduce the environmental noise affecting the converting means that record or monitor acoustic signals from the body, the adhesive patch may include an acoustic absorbing layer. The acoustic absorbing layer may be used to isolate the converting means from the external environment, reducing the environmental noise significantly.

In one embodiment of the present invention the acoustic absorbing layer may comprise a high-density material, such as a hydrocolloid material, where the hydrocolloid material may be a layer of the adhesive patch or an integral part of the adhesive patch. The isolating capabilities of the hydrocolloid material are dependent on the thickness and the chemical composition of the material, where a thicker material isolates more than a thin material and material containing high-density particles might dampen the noise and provide increased isolation. The hydrocolloid material is permeable to water vapor, which means that any water vapor introduced into the adhesive patch from the skin surface may escape the patch through the hydrocolloid layer. The water vapor permeability of the hydrocolloid material may protect the electrical circuitry within the patch such that the risk of moist damage to the electrical compounds is reduced.

In order to facilitate the acoustic transmission between the converting means and the skin surface, the adhesive patch may comprise an acoustic conducting layer. The acoustic conducting layer increases the conducting capabilities between the converting means and the skin surface, as the acoustic impedance is reduced between the layers. By reducing the acoustic impedance the conducting layer maintains the velocity of the received sound waves substantially. This means that the sound waves will cross more easily between the skin surface and the converting means, as the sound velocity of the sound waves in the conducting layer is kept close to the sound velocity within the body, by mimicking the acoustic impedance of the skin layers. Direct contact between the converting means and the skin surface might reduce the acoustic quality of the acquired signals, as the increased acoustic impedance could filter some elements of the sound when the sound crosses from the skin surface towards the converting means.

In one embodiment of the present invention the acoustic conducting layer may be formed of an acoustic conducting gel. The sound velocity of the gel is similar to the sound velocity of the skin layers. This means that the sound communicates from the skin layers via the conductive gel towards the converting means without a significant loss of quality due to the aforementioned acoustic impedance.

In one embodiment of the present invention, the acoustic conducting layer may be formed of an acoustic conducting material that may be provided as a coating that envelopes at least a part of an external surface of the converting means. The acoustic conducting material may be in the form of a solid layer enveloping a part of the external surface of the converting means or the entire external surface of the converting means. Advantageously, the acoustic conducting material covers at least the external area of the converting means that is suitable for acquiring the acoustic signal from the body.

The acoustic conducting material may envelope the entire external surface of the converting means, where the acoustic conducting material provides an increased acoustic conductivity between the converting means, the skin surface and the acoustic conducting material. Furthermore it may be used to protect or shield the converting means from any harmful contaminants that may reduce the lifespan of the converting means or may reduce the converting means capability to record acoustic signals from the body, such as particles, moisture and other contaminants that may be considered as harmful.

In one embodiment of the present invention the adhesive patch may further comprise visual means for indicating placement of the adhesive patch according to anatomic landmarks on the human or animal body. The visual means may be used to facilitate the positioning of the adhesive patch according to predetermined anatomic landmarks, where the anatomical landmarks are dependent on what acoustic monitoring task is being performed. This means that the physical positioning of the patch may facilitate for a specific type of acoustic monitoring task. This might also be important in the case were the acoustic patch has more than one converting means for recording acoustic signals from the body, for example an 1D, 2D, or 3D array of converting means and the exact placement and the spatial positioning of the array is important or even vital for the outcome of the acoustic recording, depending on the application of the adhesive patch.

The adhesive patch may further be used to monitor other acoustic signals from the body, such as respiratory signals, digestive signals, bowel signals, joint signals, urinary signals and other acoustic signals from the body.

The present invention also describes an adhesive patch kit comprising an adhesive part and a converting part. The adhesive part is a disposable part that can be thrown out after use, such that every time an adhesive part is used the adhering properties are optimal. The converting part comprises the electrical circuitry and the converting means required to record acoustic signals according to the present invention. The individual parts of the converting part, such as the converting means, transmission means and/or the processing means might be very expensive compared to the adhesive part, and by reusing the converting part multiple times it might be possible to reduce the overall cost of a single diagnostic procedure. The converting part can be secured to the adhesive part using temporary connection means, such as hook and loop connection means, adhesive means or by other mechanical connection means between the adhesive part and/or the converting part. When the adhesive part and the converting part are secured to each other, the two parts form an adhesive patch according to the present invention.

The adhesive part may be a sterile or non-sterile adhesive patch which has a first connection means for temporary connection to a second connection means provided on the converting part. Thus, the kit may be used so that the adhesive part is positioned on the skin surface of the user and where the converting part is subsequently temporarily connected to the adhesive part or by combining the adhesive part and the converting part prior to positioning the adhesive patch on the skin surface of the user. After the adhesive patch kit has been used to monitor acoustic signals from the body, the adhesive part and the converting part may be removed from the skin surface in one piece or as one part after the other. The adhesive part may subsequently be disposed in a trash bin or similar, while the converting part may be prepared for the next user by cleaning, disinfecting, refurbishing and other steps deemed advantageous by a medical professional for optimal security and/or hygiene for the next user.

The use of a disposable adhesive part ensures the adhesive qualities of the adhesive surface are optimal for application to the skin surface of the user from the start and the risk of inadvertent detachment is reduced. It is also to be understood that the adhesive part may also be a reusable part, where the adhesive surface may be of the kind that can be refurbished and prepared so that the adhesive surface has enough adhesive properties to achieve the necessary adherence to last throughout the use of the adhesive patch kit.

The present invention further describes a method for monitoring acoustic signals from the human body using an adhesive patch comprising converting means, processing means and transmission means. The adhesive patch is positioned on the skin surface of a user, such that the converting means are in direct or indirect communication with the skin surface. The converting means convert the recorded acoustic signals into an analog electrical signal, which in turn is converted into digital form using an A/D converter. In order to be able to reduce the size of the analog or digital signal, the signals are filtered using a bandpass filter having a predefined upper and lower frequency limit. The predefined upper and lower frequency limits are chosen based on what acoustic signals in the body are being monitored. In one embodiment of the present invention where the converting means comprise two microphones and the first microphone records acoustic signals from the body and the second records noise, the two resulting signals may be fed into a differential amplifier. The differential amplifier compares the input signals and reduces the magnitude of the first microphone signal by the magnitude of the synchronous second microphone signal. This results in the reduction of noise in the first microphone signal, which means that the underlying acoustic signal from the body becomes clearer in the output signal of the differential amplifier.

In one embodiment of the present invention, the output signal may be transmitted to a peripheral device using transmitting means, where further processing of the signal may be performed. In another embodiment the output signal is fed into processing means where one or more signal processing methods may be applied to the signal. The choice of methods depends on the type of acoustic signal from the body and the choice might be between methods such as time-frequency analysis, statistical analysis and other methods known in the art of signal processing. The processing means may be supplemented with analyzing means, where the processed signals or their mathematical representation may be compared to standard values, such that any deviation of standard values may be detected by the analyzing means.

At any point in time, from the acquisition of the acoustic signals using the converting means, may the resulting signals be stored in a memory bank, such as flash memory or be transmitted to a peripheral device. The choice of at which point in time storage or transmission is performed may be taken by a technician or a medical professional. Furthermore, the transmitting means may be used to program the adhesive patch and provide the patch with appropriate instructions for each monitoring task.

BRIEF DESCRIPTION OF THE DRAWINGS

The invention will now be described in further detail below with reference to the schematic drawings in which.

DETAILED DESCRIPTION

Figure 1:
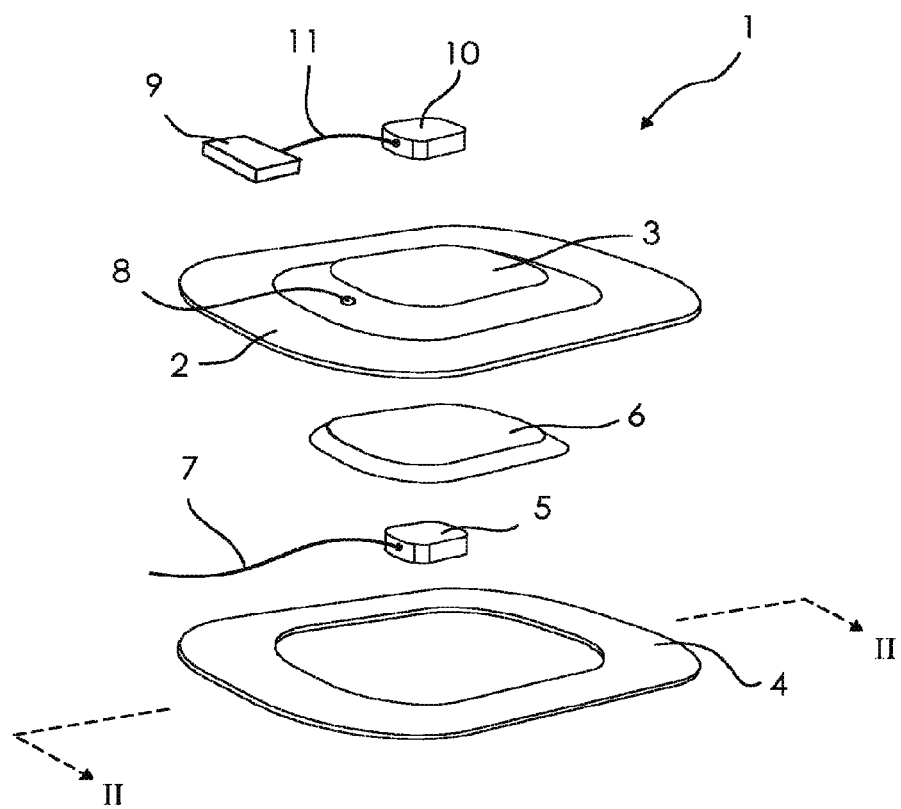
FIG. 1 is an exploded view of an adhesive patch for monitoring acoustic signals from the body according to the present invention.

FIG. 1 is an exploded view of an adhesive patch 1 for monitoring acoustic signals in the body according to the present invention. The adhesive patch 1 comprises a protective layer 2, which may also be seen as an enclosing layer. The protecting layer 2 is provided with a projection area 3, which is located substantially in the central area of the protective layer and projects axially away from the distal edges of the protective layer 2. The protective layer 2 is provided with an adhesive layer 4, which ensures that the adhesive patch 1 can be adhered to the skin surface of the subject which is to be monitored. The adhesive layer 4 extends from the distal edges of the protective layer and radially inwards towards the central area of the protective layer 2. In this embodiment the adhesive layer 4 extends from the distal area and radially inwards to the area where the projection area 3 starts.

A microphone 5 is positioned on the inner surface, i.e. the surface that is adjacent to the adhesive layer 4, of the projection area 3. This microphone 5 has, in this embodiment, direct access to the skin surface of the subject, where none of the patch layers separate the microphone and the skin surface when the adhesive patch 1 is adhered to the skin surface. This can be seen as the adhesive layer has an opening in the central area, which corresponds in size to the projection area 3. Furthermore, on the inner surface of the projection area 3, between the protective layer 2 and the microphone 5 a pad 6 or block of resilient material is placed, which provides support to the microphone 5. The resilient pad 6 ensures that the microphone is optimally pressed to the skin surface when the patch adhered on the skin surface of the user. The choice of resilient material for the pad 6 may be varied, such that the contact between the skin surface and the microphone is always at an optimal pressure in different situations.

The microphone 5 is in electrical communication with a controlling unit 9 via an electrical lead 7, which is fed through a small opening 8 in the protective layer 2, to the external surface of the protective layer 2. In this view the electrical lead 7 is not connected to the controller unit 9, but in an assembled state the lead is connected and in communication with the controller unit 9. The opening 8 is large enough for the lead to pass through, but small enough to ensure a snug fit, such that excessive noise does not pass through the hole to interfere with the recordings made by the microphone 5.

In one embodiment the controller unit 9 may be permanently connected to the protective layer 2, while in another embodiment the controller unit 9 may be temporarily connected to the external surface of the protective layer 2, such that the controller unit 9 may be removed if the protective layer 2 is to be discarded. In this embodiment of the present invention, a second microphone 10 is placed on the external surface of the protective layer 2, where the second microphone 10 is used to record environmental noise, from the surrounding environment. The second microphone 10 is in electrical communication with the controller unit via an electrical lead 11.

In another embodiment of the adhesive patch the protective layer 2 might be an adhesive material, which means that no specific adhesive layer 4 is needed to adhere the patch to the skin surface of the user. In this case, the outer surface of the patch may be provided with a protecting film, such that the outer surface of the adhesive patch 1 is not adhesive.

Figure 2:
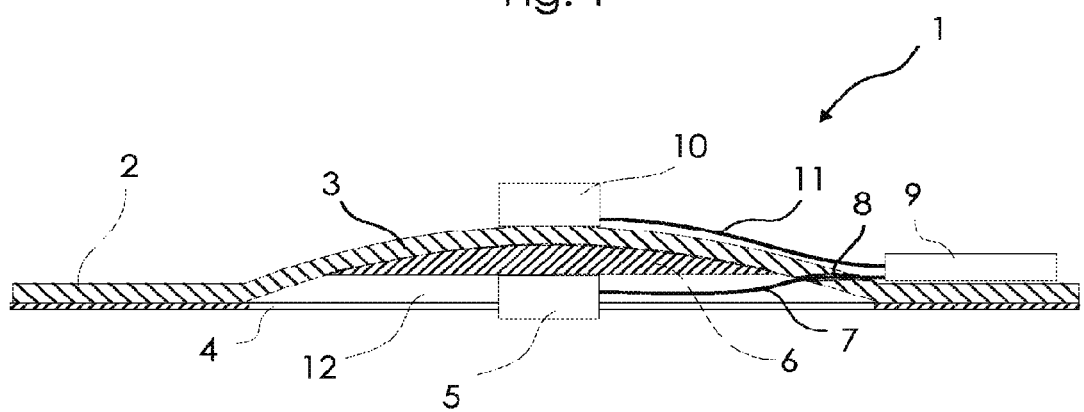
FIG. 2 is a sectional view of the same taken along line II-II in FIG. 1

FIG. 2 shows a sectional view of the adhesive patch 1 taken along line II-II in FIG. 1, where the different parts of the adhesive patch are assembled. It can be seen in this assembled state that the first microphone 5, protrudes from a plane defined by the adhesive layer 4, such that when the patch is adhered to the skin surface, the microphone becomes depressed into the skin surface and the resilient pad 6 and the pad 6 provides optimal pressure between the first microphone 5 and the skin surface.

Furthermore, in this configuration, the first microphone 5 is in electrical communication with the controller unit 9 where an electrical lead 7 passes through opening 8 from the inner volume 12 of the patch to the external surface of the patch.

In the present invention, the controller unit 9, comprises the electrical circuitry necessary to convert, process, transmit, store and analyze the electrical signals acquired from the first 5 and the second microphone 10. The electrical circuitry for processing the signals may be chosen from the group of: a filter component, an A/D converter, a microprocessor, a wireless transmission module, a flash memory chip, a USB controller or similar electronic components known in the art. The controller unit 9 may further be provided with an on/off switch, which may be used to trigger the adhesive patch into a functional state or out of a functional state to a passive state.

Furthermore, the controller unit 9 comprises a power source, such as a single use or a rechargeable battery, kinetic power converter or similar in order to provide electrical current to the electrical circuitry and the electrical or electronic components of the adhesive patch.

Figure 3:
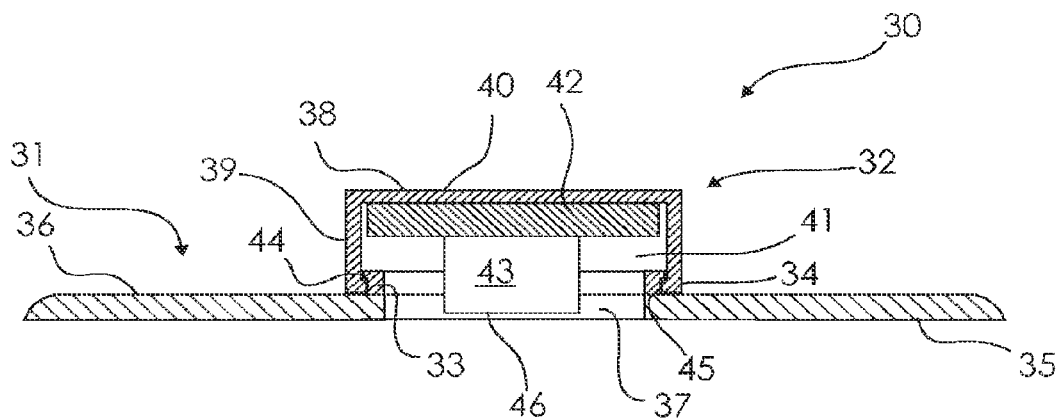
FIG. 3 is a sectional view of an adhesive patch comprising an adhesive part and a separate converting part.

FIG. 3 shows a schematical view of one embodiment of an adhesive patch 30 according to the present invention where the adhesive part 31 and the converting part 32 may be releasably connected to each other via a first connecting means 33 and a second connecting means 34. The adhesive part 31 is provided with an adhesive surface 35 providing the skin contacting surface and a non-adhesive outer surface 36 which faces away from the skin contacting surface 35. The adhesive part has a through-going opening 37 which provides communication from the outer surface 36 of the adhesive part 31 to the skin contacting surface 35.

The converting part 32 comprises a housing 38 having a cylindrical wall 39 and a back wall 40 where the walls define an inner cavity 41 housing a pressure management element 42, in the form of resilient foam or similar material, and converting means 43 in the form of a microphone or a sound transducer. The converting part 32 may be connected to the first connecting means 33, which is in the form of a coupling ring, encircling the opening 37, where the ring 33 is permanently attached to the outer surface 36 of the adhesive part 31. The free end of the housing 38 is provided with a second connecting means 34 in the form of a first radial protrusion 44 that is capable of snap locking into a second protrusion 45 that is provided as a protrusion 45 or a rim on the free end of the coupling ring 33. As the converting part is attached to the adhesive part, the skin contacting surface 46 of the converting means 43 is substantially parallel to the skin contacting surface of the adhesive part 31, which means that the converting part comes into contact with the skin surface as the adhesive patch 40 is attached to the skin surface of the user. Any modifications to the size, shape, material choice are obvious to the skilled person based on the teachings of the present invention.

Figure 4A:
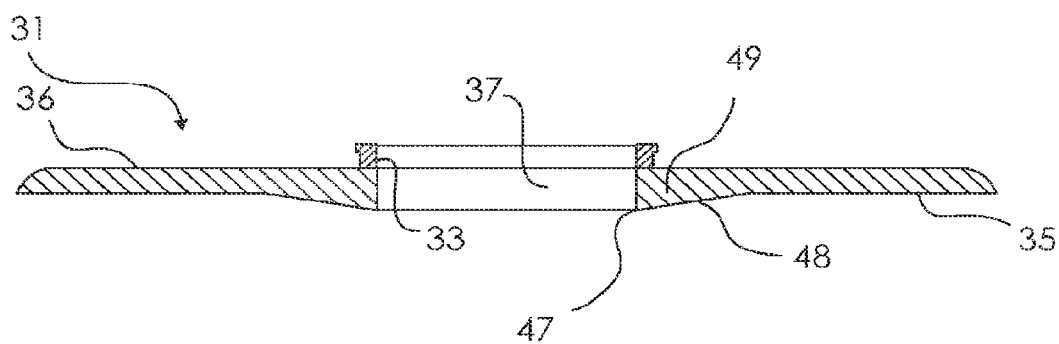
FIGS. 4a and 4b are sectional views of adhesive parts having compression structures.

FIG. 4a shows a schematical view of an adhesive part 31 having a compression structure 47 on the skin contacting surface 35 of the adhesive part 31. The compression structure 47 is formed as a tapered surface area 48 of the skin contacting surface 35 which protrudes in a direction away from the adhesive part 31. The tapered surface may be seen as an increase in thickness of the adhesive part 31 where the adhesive part is thinner in the area in a radial direction away from the opening 37 and increases in thickness the closer the area 49 is to the opening 37.

Figure 4B:
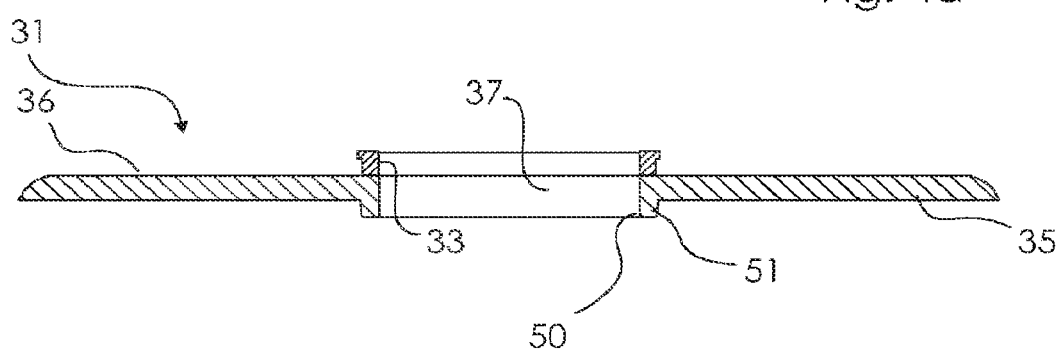

FIG. 4b shows a schematical view of an adhesive part 31 having a compression structure 50 in the form of a circular protrusion 51 on the skin contacting surface 35 of the adhesive part 31.

Figure 5:
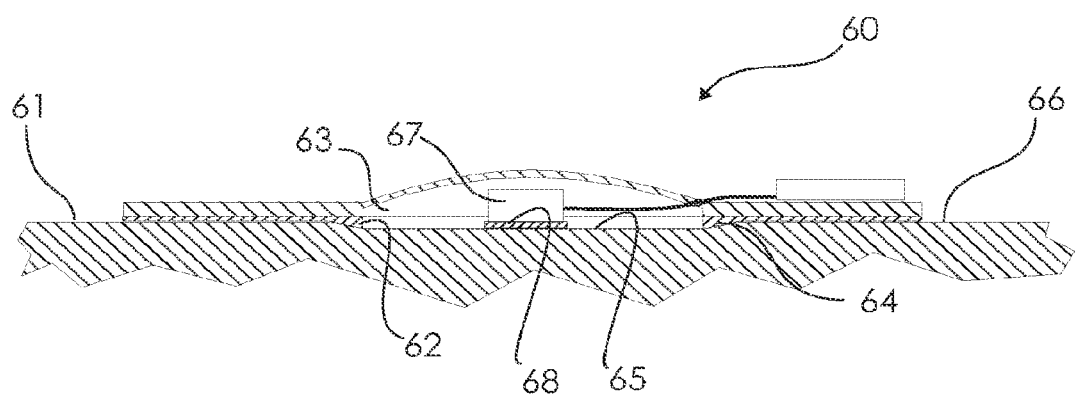
FIG. 5 is a sectional view of an adhesive patch according to the present invention applied on the skin surface of a user.

FIG. 5 shows an adhesive patch 60 according to the present invention applied on the skin surface 61 of a user, having a compression structure 62 as shown in FIG. 4a, where the compression structure 62 encircles the opening 63 and the tapered surface 64 or the protrusion shown in FIG. 4b increases the surface tension and/or stretches the skin surface 65 inside the opening 63 of the user upon application of the adhesive patch 60 and maintain the tension on the skin surface 63 during the continued application of the adhesive patch 60. In this embodiment, it may be seen that even if the skin surface 66 surrounding the adhesive patch 60 is stretched, deformed or moved in any way, the surface tension of the skin surface 65 inside the opening 63 is maintained, and thus the pressure between the converting means 67 and the skin surface 65 is managed. In this embodiment, a layer of acoustic conducting layer 68 is applied between the skin surface 64 and the converting means 67.

The acoustic conducting layer 68, may in some embodiments stretch throughout the entire opening 63 or just a part of the opening. The layer 68 may be a layer having an adhesive skin contacting surface and have an adhesive layer on the opposite surface. The layer 68 may be a gel like layer or in some embodiments it may be a layer of a gas, such as air. Any suitable acoustic conducting material known in the art may be used to facilitate acoustic transmission or transfer between the skin surface and the converting means.

The embodiments shown in FIGS. 4 and 5 are shown as being a part of a two-part device, where the converting part can be releasably connected to the adhesive part. In other embodiments having the same or similar compression structure, the adhesive part may be permanently connected to the converting part, such as shown in the embodiment of FIG. 2.

Any modification made in the shape, form, size and structure of the compression structure shown in FIGS. 4 and 5 to obtain similar or the same functionality is obvious to the skilled person based on the present disclosure.

The invention claimed is:

1. An adhesive patch for monitoring acoustic signals from a human or animal body comprising:
    an adhesive part and a converting part being releasably connected to each other whereby each may be separated from the other so that one may be discarded and the other reused;
    wherein the adhesive part is provided with an adhesive surface adapted for providing a skin contacting surface, and the adhesive part has a through-going opening whereby communication through the adhesive part to the skin contacting surface is provided; and
    the converting part comprises a converting means comprising:
        a first microphone having a skin contacting surface, the first microphone configured to record body acoustic signals and convert them to body output signals;
        a second microphone mounted to record environmental noise from an environment surrounding the adhesive patch and converting the recorded noise to a noise output signal; and
        a controller unit that is configured to receive the body output signals, remove any environment noise from the body output signals by processing the body output signals with the noise output signal to form a controller output signal, and transmit the controller output signal to a peripheral device;
    wherein when the converting part is connected to the adhesive part, the converting means is arranged in the opening of the adhesive part such that the skin contacting surface of the first microphone and the skin contacting surface of the adhesive part both come into contact with a skin surface as the adhesive patch is attached to a skin surface of a user, and
    wherein the adhesive part is also provided with a compression structure at the skin contacting surface of the adhesive part, wherein the compression structure is in the form of at least one protrusion that projects out from the skin contacting surface and is positioned around the first microphone.

2. The adhesive patch according to claim 1, wherein the first and second microphones are configured to record synchronously and the controller unit comprises an amplifier that is configured to receive and compare the body output signals with the synchronous noise output signals and reduce the magnitude of the body output signals by at least part of the magnitude of the compared synchronous noise output signals.

3. The adhesive patch of claim 2 wherein the controller unit further comprises an on/off switch, which is used to trigger the adhesive patch into a functional state or out of a functional state to a passive state.

4. The adhesive patch according to claim 1, wherein the controller unit comprises electrical circuitry for processing the signals from the first and second microphones, and includes at least one of the following elements: a filter component, an A/D converter, a microprocessor, a wireless transmission module, a flash memory chip, and a USB controller.

\* \* \* \* \*